US00PP35392P2

(12) United States Plant Patent
Spil

(10) Patent No.: US PP35,392 P2
(45) Date of Patent: Sep. 19, 2023

(54) ***ANEMONE* PLANT NAMED 'IFANFRAP'**

(50) Latin Name: *Anemone hupehensis*
Varietal Denomination: IFANFRAP

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/100,191

(22) Filed: Jan. 23, 2023

(51) Int. Cl.
*A01H 5/02* (2018.01)
*A01H 6/72* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. Anne Whealy

(57) ABSTRACT

A new and distinct cultivar of *Anemone* plant named 'IFANFRAP', characterized by its upright and uniform plant habit; moderately vigorous to vigorous growth habit; early and freely flowering habit; long flowering period; large semi-double flowers that are white in color; and good garden performance.

2 Drawing Sheets

Figure 1:
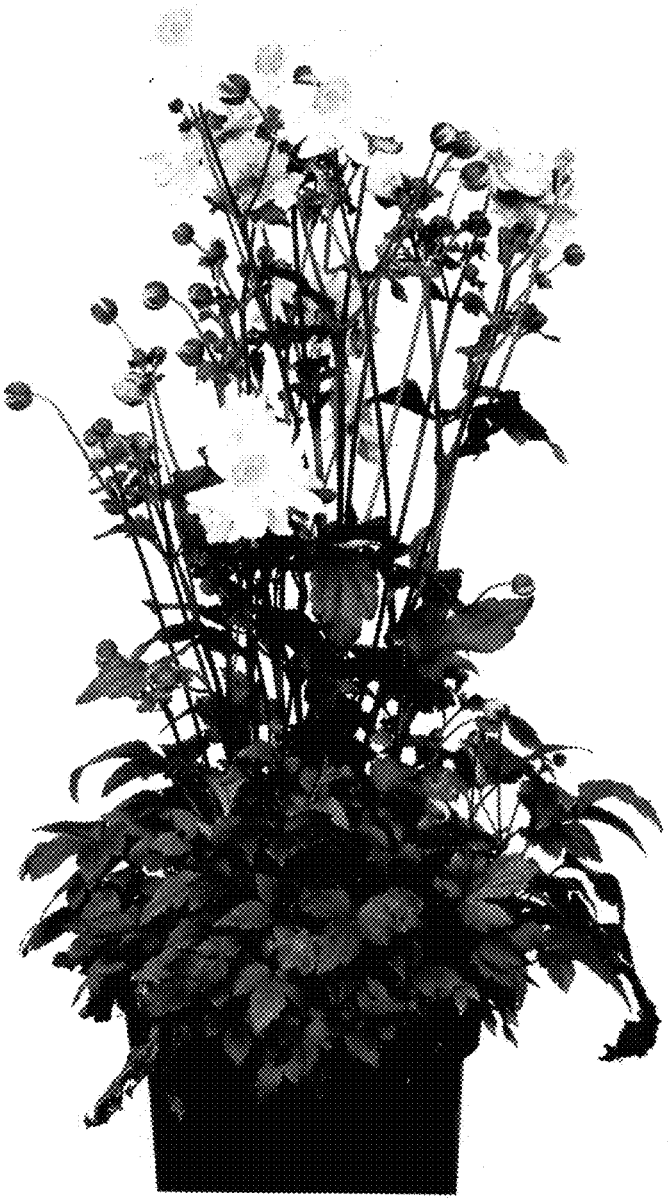

Botanical designation: *Anemone hupehensis*.
Cultivar denomination: 'IFANFRAP'.

STATEMENT REGARDING PRIOR DISCLOSURES BY APPLICANT

An European Plant Breeder's Rights application for the instant plant was filed by the Applicant on Nov. 22, 2022, application number 2022/2619. Foreign priority is not claimed to this application.

BACKGROUND OF THE INVENTION

The present invention relates to a new and distinct cultivar of *Anemone*, botanically known as *Anemone hupehensis* and hereinafter referred to by the name 'IFANFRAP'.

The new *Anemone* plant is a product of a planned breeding program conducted by the Inventor in Heerhugowaard, The Netherlands. The objective of the breeding program is to create new vigorous and fast-growing *Anemone* plants with numerous attractive flowers.

The new *Anemone* plant originated from an open-pollination in July, 2017 in a controlled greenhouse environment in Heerhugowaard, The Netherlands of *Anemone hupehensis* 'IFANSA', disclosed in U.S. Plant Pat. No. 31,802, as the female, or seed, parent with an unknown proprietary selection of *Anemone hupehensis* as the male, or pollen, parent. The new *Anemone* plant was discovered and selected by the Inventor as a single flowering plant within the progeny of the stated open-pollination in a controlled greenhouse environment in Heerhugowaard, The Netherlands in August, 2018.

Asexual reproduction of the new *Anemone* by in vitro meristem culture in a controlled environment in Heerhugowaard, The Netherlands since April, 2019 has shown that the unique features of this new *Anemone* plant are stable and reproduced true to type in successive generations.

SUMMARY OF THE INVENTION

Plants of the new *Anemone* have not been observed under all possible combinations of environmental conditions and various cultural practices. The phenotype may vary somewhat with variations in environmental conditions such as temperature and light intensity without, however, any variance in genotype.

The following traits have been repeatedly observed and are determined to be the unique characteristics of 'IFANFRAP'. These characteristics in combination distinguish 'IFANFRAP' as a new and distinct *Anemone* plant:

1. Upright and uniform plant habit.
2. Moderately vigorous to vigorous growth habit.
3. Early and freely flowering habit.
4. Long flowering period.
5. Large semi-double flowers that are white in color.
6. Good garden performance.

Plants of the new *Anemone* can be compared to plants of the female parent, 'IFANSA'. Plants of the new *Anemone* differ primarily from plants of 'IFANSA' in the following characteristics:

1. Plants of the new *Anemone* are not as compact as plants of 'IFANSA'.
2. Plants of the new *Anemone* are more vigorous than plants of 'IFANSA'.

Plants of the new *Anemone* can be compared to plants of *Anemone hupehensis* 'Frilly Knickers', not patented. In side-by-side comparisons, plants of the new *Anemone* and 'Frilly Knickers' differ primarily in plant habit as plants of the new *Anemone* are more compact than plants of 'Frilly Knickers'.

Plants of the new *Anemone* can also be compared to plants of *Anemone hupehensis* 'Dreaming Swan', not patented. In side-by-side comparisons, plants of the new *Anemone* and 'Dreaming Swan' differ primarily in plant habit as plants of the new *Anemone* are more compact and shorter than plants of 'Dreaming Swan'.

BRIEF DESCRIPTION OF THE PHOTOGRAPHS

The accompanying colored photographs illustrate the overall appearance of the new *Anemone* plant showing the colors as true as it is reasonably possible to obtain in colored reproductions of this type. Colors in the photographs may differ slightly from the color values cited in the detailed botanical description which accurately describe the colors of the new *Anemone* plant.

The photograph on the first sheet (FIG. 1) is a side perspective view of a typical plant of 'IFANFRAP' grown in a container.

Figure 2:
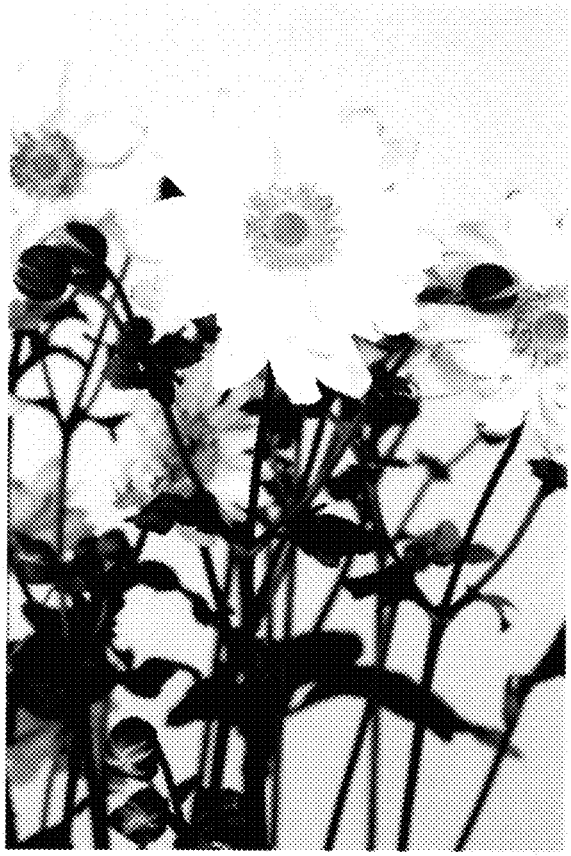

The photograph at the top of the second sheet (FIG. 2) is a close-up view of typical flowers of 'IFANFRAP'.

Figure 3:
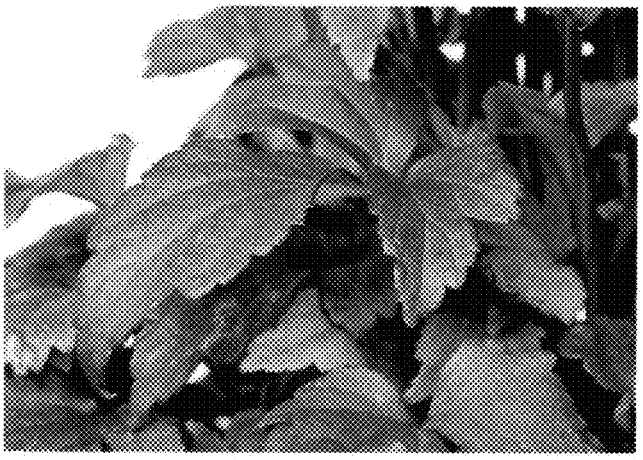

The photograph at the bottom of the second sheet (FIG. 3) is a close-up view of typical leaves of 'IFANFRAP'.

DETAILED BOTANICAL DESCRIPTION

The aforementioned photographs and following observations, measurements and values describe plants grown during the late summer/early autumn in 17-cm containers in an outdoor nursery in Heerhugowaard, The Netherlands and under cultural practices typical of commercial *Anemone* production. During the production of the plants, day temperatures ranged from 16° C. to 30° C. and night temperatures ranged from 8° C. to 18° C. Plants were 16 weeks old when the photographs and description were taken. In the following description, color references are made to The Royal Horticultural Society Colour Chart, 2015 Edition, except where general terms of ordinary dictionary significance are used.

Botanical classification: *Anemone hupehensis* 'IFANFRAP'.

Parentage:

*Female, or seed, parent.*—*Anemone hupehensis* 'IFANSA', disclosed in U.S. Plant Pat. No. 31,802.

*Male, or pollen, parent.*—Unknown selection of *Anemone hupehensis*, not patented.

Propagation:

*Type.*—In vitro meristem culture.

*Time to initiate roots, summer.*—About ten days at temperatures about 22° C.

*Time to initiate roots, winter.*—About 15 days at temperatures about 20° C.

*Time to produce a rooted young plant, summer.*—About 42 days at temperatures about 20° C.

*Time to produce a rooted young plant, winter.*—About 50 days at temperatures about 20° C.

*Root description.*—Thin, fibrous; typically light brown in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Herbaceous perennial; upright and uniform plant habit with basal stems and leaves developing in basal rosettes; numerous basal rosettes developing per plant; plants ovate in overall shape; moderately vigorous to vigorous growth habit; moderate growth rate.

*Plant height, soil level to top of foliar plane.*—About 35.4 cm.

*Plant height, soil level to top of floral plane.*—About 49.8 cm.

*Plant diameter.*—About 33.3 cm.

Branch description:

*Quantity per plant.*—About 14.

*Length.*—About 26.1 cm.

*Diameter.*—About 4 mm.

*Internode length.*—About 17.9 cm.

*Strength.*—Moderately strong.

*Aspect.*—Upright to about 5° from vertical.

*Texture and luster.*—Sparsely to moderately pubescent; moderately glossy.

*Color, developing.*—Close to 144A; surfaces exposed to full sun, variably tinged with close to N186C.

*Color, developed.*—Close to 148A; proximally, close to 144A; surfaces exposed to full sun, variably tinged with close to 200B.

Leaf description:

*Arrangement, basal leaves.*—Alternate; compound.

*Arrangement, cauline leaves.*—Opposite; simple or compound.

*Length, basal leaves.*—About 8.8 cm.

*Width, basal leaves.*—About 7 cm.

*Length, cauline leaves.*—About 7.6 cm.

*Width, cauline leaves.*—About 6.1 cm.

*Length, basal and cauline leaflets.*—Terminal leaflets, about 7.3 cm and lateral leaflets, about 5.1 cm.

*Width, basal and cauline leaflets.*—Terminal leaflets, about 6.1 cm and lateral leaflets, about 3.1 cm.

*Shape, basal and cauline leaves.*—Palmately three-lobed to trifoliate; lobed to cleft, depth of sinuses are medium to deep and convergent; in overall outline, leaves are broadly ovate; slightly carinate and slightly reflexed.

*Shape, basal and cauline leaflets.*—Ovate to elliptic.

*Apex, basal and cauline leaflets.*—Acute.

*Base, basal and cauline leaflets.*—Truncate to hastate or obtuse.

*Margin, basal and cauline leaflets.*—Biserrate.

*Texture and luster, basal and cauline leaflets, upper surface.*—Sparsely pubescent; slightly rugose; slightly glossy.

*Texture and luster, basal and cauline leaflets, lower surface.*—Moderately pubescent; slightly rugose; matte.

*Venation pattern, basal and cauline leaflets.*—Laciniate.

*Color, basal and cauline leaflets.*—Developing leaflets, upper surface: Close to 144B. Developing leaflets, lower surface: Close to 146D. Fully expanded leaflets, upper surface: Close to NN137A; venation, close to N144A; in the autumn, close to between 187A and 200B. Fully expanded leaflets, lower surface: Close to between 191A and 191B; venation, close to N144A; in the autumn, close to between N148C and 195A.

*Leaf petioles.*—Length, basal leaves: About 9 cm. Diameter, basal leaves: About 1.5 mm. Length, cauline leaves: About 3 cm. Diameter, cauline leaves: About 1.5 mm. Strength, basal and cauline leaves: Strong. Texture and luster, basal and cauline leaves, upper and lower surfaces: Moderately to densely pubescent; slightly glossy. Color, basal and cauline leaves, upper surface: Close to 146A. Color, basal and cauline leaves, lower surface: Close to 144A.

Flower description:

*Flower arrangement and flowering habit.*—Semi-double type rotate flowers arranged in terminal compound cymes; freely flowering habit with nine flowers per inflorescence and about 125 flowers developing per plant during the flowering season; flowers face upright to slanting outwardly.

*Fragrance*.—None detected.

*Natural flowering season*.—Plants of the new *Anemone* flower during the late summer into the autumn in The Netherlands.

*Flower longevity*.—Individual flowers last about ten days on the plant; flowers not persistent.

*Inflorescence height*.—About 25.2 cm.

*Inflorescence diameter*.—About 16.5 cm.

*Flower diameter*.—About 7.1 cm.

*Flower length* (*depth*).—About 3.5 cm.

*Flower buds*.—Length: About 1.2 cm. Diameter: About 1.2 cm. Shape: Roughly spherical. Texture and luster: Slightly pubescent; matte. Color: Close to between N186C and 187A; proximally, close to 144C.

*Petals*.—Absent.

*Sepals*.—Quantity and arrangement: About five, occasionally six, arranged in two whorls. Length, lower whorl: About 1.8 cm. Length, upper whorl: About 3 cm. Width, lower whorl: About 1.25 cm. Width, upper whorl: About 1.45 cm. Shape, lower whorl: Broadly ovate to broadly elliptic; moderately concave. Shape, upper whorl: Elliptic to obovate; slightly concave. Apex, lower and upper whorls: Bluntly acute to obtuse. Base, lower and upper whorls: Cuneate. Margin, lower and upper whorls: Entire; not undulate to slightly undulate. Texture and luster, upper and lower whorls, upper surface: Smooth, glabrous; moderately velvety; not rugose; slightly glossy. Texture and luster, upper and lower whorls, lower surface: Densely pubescent; not rugose; slightly glossy. Color: When opening, lower whorl, upper surface: Close to 76D; towards the margins, close to 77D; moderately tinged with close to 148D. When opening, upper whorl, upper surface: Close to NN155A; towards the margins and apex, close to 76B to 76C; margin edge, close to N78B; towards the base, tinged with close to 145C to 145D. When opening, lower whorl, lower surface: Close to N186D; towards the base, close to 147C. When opening, upper whorl, lower surface: Close to NN155A strongly flushed and tinged with close to N77B; towards the base, tinged with close to 145C to 145D. Fully opened, lower whorl, upper surface: Close to 147C slightly tinged with close to 76D and N77B; venation, similar to lamina colors; color does not change with subsequent development. Fully opened, upper whorl, upper surface: Close to N155A tinged with close to 147D and 186D; venation, similar to lamina colors; color does not change with subsequent development. Fully opened, lower whorl, lower surface: Close to N186C tinged with close to 147B; venation, similar to lamina color; color does not change with subsequent development. Fully opened, upper whorl, lower surface: Close to N155A strongly flushed and tinged with close to N77B and N186D; venation, similar to lamina colors; color does not change with subsequent development.

*Sepaloids*.—Quantity and arrangement: About 31 arranged in two whorls. Length: About 3.5 cm. Length: About 1.3 cm. Shape: Obovate to elliptic. Apex: Bluntly acute to obtuse. Base: Narrowly cuneate. Margin: Entire; slightly and coarsely undulate. Texture and luster, upper surface: Smooth, glabrous; moderately velvety; not rugose; slightly glossy. Texture and luster, lower surface: Densely pubescent; not rugose; slightly glossy. Color: When opening, upper surface: Close to 155C; towards the base, close to 157A to 157D; towards the margins and apex, slightly flushed with close to 76B to 76C. When opening, lower surface: Close to 155C; towards the base, close to 157C to 157D; towards the apex, slightly flushed with close to N75B to N75C. Fully opened, upper surface: Close to N155B; towards the margins and apex, tinged with close to 76C; venation, similar to lamina color; color; color does not change with subsequent development. Fully opened, upper surface: Close to NN155A; towards the margins and apex, tinged with close to 77C and N77B; venation, similar to lamina color; color; color does not change with subsequent development.

*Peduncles*.—Length: About 14.2 cm. Diameter: About 2.5 mm. Aspect: About 22.5° from lateral branch axis. Strength: Strong. Texture and luster: Moderately to densely pubescent; moderately glossy. Color: Close to 146A; surfaces exposed to sunlight are strongly tinged with close to 200B.

*Pedicels*.—Length: About 10.3 cm. Diameter: About 2 mm. Aspect: Upright to about 40° from the peduncle axis. Strength: Moderately strong. Texture and luster: Densely pubescent; slightly glossy. Color: Close to 146A; distally, close to 145A to 145B; surfaces exposed to sunlight are strongly tinged with close to 200B to 200C.

*Reproductive organs*.—Androecium: Stamen number per flower: About 200. Filament length: About 6 mm. Filament color: Close to 155A. Anther shape: Oblong. Anther size: About 1 mm by 2 mm. Anther color: Close to 13A. Amount of pollen: Moderate. Pollen color: Close to 11D. Gynoecium: Pistil number per flower: About 400. Pistil length: About 0.75 mm. Stigma shape: Club-shaped. Stigma size: About 0.2 mm by 0.2 mm. Stigma color: Close to 151C. Style length: About 0.55 mm. Style color: Close to 144C. Ovary color: Close to 145D.

*Seeds and fruits*.—To date, seed and fruit development have not been observed on plants of the new *Anemone*.

Garden performance: Plants of the new *Anemone* have been observed to have good garden performance and to tolerate temperatures ranging from about −30° C. to about 35° C. and to be suitable for USDA Hardiness Zones 4 through 9.

Pathogen & pest resistance: To date, plants of the new *Anemone* have not been observed to be resistant to pathogens and pests common to *Anemone* plants.

It is claimed:

1. A new and distinct *Anemone* plant named 'IFANFRAP' as illustrated and described.

* * * * *